United States Patent [19]

Lichtenwalter

[11] Patent Number: 5,683,875
[45] Date of Patent: Nov. 4, 1997

[54] METHOD FOR DETECTING A TARGET NUCLEIC ACID ANALYTE IN A SAMPLE

[75] Inventor: Kay Lichtenwalter, San Jose, Calif.

[73] Assignee: Hewlett-Packard Company, Palo Alto, Calif.

[21] Appl. No.: 434,112

[22] Filed: May 4, 1995

[51] Int. Cl.⁶ ............... C12Q 1/68; C12Q 1/70; C12P 19/34; C07H 21/04
[52] U.S. Cl. .................. 435/6; 435/5; 435/91.1; 435/91.2; 435/173.9; 536/24.3; 536/24.32; 536/24.33; 210/360; 422/186.03
[58] Field of Search ............... 435/5, 6, 91.2, 435/91.1, 173.9; 536/24.3–24.33; 210/360; 422/186.03; 204/156

[56] References Cited

U.S. PATENT DOCUMENTS

| | | | |
|---|---|---|---|
| 4,233,169 | 11/1980 | Beall et al. | 252/62.59 |
| 4,672,040 | 6/1987 | Josephson . | |
| 4,959,463 | 9/1990 | Froehler et al. | 536/27 |
| 5,200,314 | 4/1993 | Urdea | 435/6 |
| 5,387,510 | 2/1995 | Wu | 435/91.2 |
| 5,437,978 | 8/1995 | Ubukata et al. | 435/6 |
| 5,545,540 | 8/1996 | Mian | 435/91.2 |

FOREIGN PATENT DOCUMENTS

| | | |
|---|---|---|
| 0 288 737 | 11/1988 | European Pat. Off. . |
| 0 265 244 | 9/1992 | European Pat. Off. . |
| 2194176 | 3/1988 | United Kingdom . |
| WO 90/06045 | 6/1990 | WIPO . |
| WO 93/25709 | 12/1993 | WIPO . |

OTHER PUBLICATIONS

Lund et al. Nucleic Acids Research 16: 10861–10880 1988.

*Primary Examiner*—W. Gary Jones
*Assistant Examiner*—Dianne Rees

[57] ABSTRACT

A method is provided for detecting a target nucleic acid analyte in a sample. The method involves preparing an immobilized capture oligonucleotide that is complementary to the target analyte using a magnetic cycling method, incubating the sample with the immobilized capture oligonucleotide to capture the target analyte thereby forming a capture oligonucleotide-analyte complex, and detecting the presence of the capture oligonucleotide-analyte complex.

8 Claims, No Drawings

METHOD FOR DETECTING A TARGET NUCLEIC ACID ANALYTE IN A SAMPLE

TECHNICAL FIELD

This invention relates generally to synthesis of immobilized oligonucleotides using magnetic cycling. More particularly, the invention relates to methods of providing immobilized oligonucleotides which may be used in diagnostic assays to detect the presence of target nucleotide sequences.

BACKGROUND

The ability to clone and synthesize nucleotide sequences has led to the development of a number of highly effective techniques in disease diagnosis and genetic analysis. Particularly, the detection of DNA or RNA sequences associated with a particular antigen, phenotype or genotype currently enjoys widespread use in modem medicine. These clinical techniques generally involve hybridization between a probe and a complementary target nucleotide sequence, offering a convenient and reliable means for the isolation, identification and analysis of nucleotides. Typical methods involve either hybridization with a sample or probe nucleotide sequence immobilized to a solid support (mixed phase hybridization), or hybridization of sample and probe sequences in solution, followed by a separation of hybridized and unhybridized species. See, e.g., Meinkoth et al. (1984) *Anal. Biochem.* 138:267–284.

A number of mixed-phase hybridization techniques are well known in the art. Commonly used solid supports include nitrocellulose or nylon, and the methods of immobilizing nucleotides (e.g., DNA) to such supports include transfer of selected sequences onto nitrocellulose filters or nylon membranes using Southern blot, colony and plaque blot, or dot and slot blot techniques. Leary et al. (1983) *Proc. Natl. Acad Sci. USA* 80:4045–4049. However, an oft-encountered problem in DNA transfer techniques arises from the fact that the DNA is noncovalently attached to the support, leading to a significant loss of the DNA and resulting in only a small mount of DNA being available for hybridization.

Thus, a number of chemical methods have been described for attachment of DNA to solid supports via stable covalent linkages. Particularly, carbodiimide may be used for end-attachment of DNA to cellulose, SEPHADEX® or SEPHACRYL®. See, e.g., Gilham, P. T. (1968) *Biochemistry* 2:2809–2813, Rickwood, D. (1972) *Biochem. Biophys. Acta* 269:47–50 and Bunemann et al. (1982) *Nucl. Acids Res.* 10:7163–7180. DNA may also be immobilized via reaction of its bases with activated supports such as CNBr-activated agarose or diazotized SEPHACRYL®. Arndt-Jovin et al. (1975) *Eur. J. Biochem.* 54:411–418.

However, use of the above described methods to immobilize probes is limited by a number of substantial deficiencies in the context of clinical nucleotide analysis techniques. Particularly, support materials such as agarose or cellulose generally have a low surface-to-volume ratio. This feature leads to poor hybridization kinetics—thereby reducing the sensitivity of the hybridization assay—as well as significantly increasing the mount of time required to carry out the technique.

Further, even though immobilization of DNA by reaction of its bases with an activated surface (e.g., with a CNBr-activated support) is relatively easy to carry out, all of the bases which are used to immobilize the DNA become incapable of base pairing, thereby greatly reducing hybridization efficiency of the immobilized support. End attachment of long polynucleotides via their 5'-phosphate termini to cellulose and SEPHACRYL® is also notoriously inefficient. Lund et al. (1988) *Nucl. Acids Res.* 16(22):10861–10880. Accordingly, there remains a need to provide an improved method of covalently immobilizing oligonucleotide probes to a support for use in hybridization assays. Further, attachment of the oligonucleotide to the support should yield a moiety capable of mixed-phase hybridization kinetics which equal or approach the kinetics of the corresponding hybridization in solution.

In this regard, particulate support structures having a higher surface-to-volume ratio and which may be kept in a homogeneous solution during hybridization have been developed. Use of such support structures enables better hybridization kinetics than previously possible. These particulate supports include latex and dextran particles which are compatible with covalent attachment techniques. See, e.g., Wolf et al. (1987) *Nucl. Acids Res.* 15:2911–2926 and Gingeraas et al. (1987) *Nucl. Acids Res.* 15:5373–5390. Magnetic particles have also been suggested for use in the synthesis of organic compounds, including oligomers such as DNA and RNA, as well as in other techniques such as nucleic acid hybridization. Magnetic particles provide an easily retrievable support system for target capture and background removal and have been indicated in a number of automated techniques.

However, despite several advances in nucleic acid technology, clinical hybridization reactions still suffer from inadequate reaction kinetics, resulting in lengthy, time-consuming techniques. These methods entail a number of washing steps and/or other manipulations to avoid non-specific nucleotide binding and other sources of background noise, necessitating copious technician interaction. Present hybridization techniques are also limited in that the degree of specificity and sensitivity currently attainable is much less than that which is deemed desirable in clinical diagnosis. Finally, the continued use of inadequate primer-to-support attachment methods leads to the possibility of obtaining false-positive or negative results, greatly reducing the usefulness of such techniques in the clinical setting.

Accordingly, there remains a great deal of interest in developing improved methods of nucleic acid analysis which would limit the amount of physical manipulations necessary, reduce assay time and provide for enhanced specificity and sensitivity.

RELATED ART

Other methods of synthesizing oligonucleotides or isolating or separating oligonucleotides using magnetically responsive particles have been reported and are exemplified by the following:

International Publication No. WO 90/06045, published 14 Jun. 1990, describes a method of preparing DNA using magnetic beads coated with oligonucleotides (which serve as hybridization probes) to form a magnetic bead/probe complex. The magnetic beads, and any bound nucleic acid, may be magnetically separated from the sample.

U.K. Patent Application GB 2194176, published 2 Mar. 1988, describes an apparatus for assembling oligomers using a solid support on which the growing oligomer is chemically bonded, wherein the solid support may be associated with a ferromagnetic material to facilitate automated handling.

Lund et al. (1988) *Nucl. Acids Res.* 16(22):10861–10880 describe a number of methods of covalent attachment of DNA or oligonucleotides to magnetic, monosized beads and further report on the kinetics of hybridizations using DNA-bead complexes.

U.S. Pat. No. 4,672,040, issued 9 Jun. 1987 to Josephson, describes the use of magnetically responsive particles in methods of separating molecules such as specific nucleotide sequences from biological samples and the like.

European Patent Application 0 288 737, published 2 Nov. 1988, describes nucleic acid hybridization assays using probe sequences immobilized on water suspensible particles.

International Publication No. WO 93/25709, published 23 Dec. 1993, describes a method of separating nucleic acid sequences from a sample by contacting a probe sequence immobilized to a magnetic particle with the sample, allowing hybridization of complementary sequences and separating the hybrids from the sample by magnetic attraction.

European Patent No. 0 265 244, dated 23 Sep. 1992, describes methods and kits for capturing target oligonucleotides from clinical samples wherein magnetic particles are used as retrievable supports for target capture and background removal.

SUMMARY OF THE INVENTION

In accordance with an embodiment of the invention, a method is provided for synthesizing immobilized capture oligonucleotides. The method entails contacting a template oligonucleotide linked to a retrievable particle with a primer oligonucleotide immobilized to a substrate and incubating the oligonucleotides under suitable hybridizing conditions to form a template-primer complex. A polynucleotide polymerase is then added to the complex under suitable polymerizing conditions whereby the primer is extended to provide an immobilized duplex. The duplex is disrupted by retrieving the retrievable particle, leaving an elongated capture oligonucleotide immobilized to the substrate. The capture oligonucleotide may then be used in highly specific and sensitive hybridization assays, such as in hybridization assays for detection of target nucleic acids in a clinical diagnosis or the like.

In another embodiment, a method is provided for synthesizing an expanded population of immobilized capture oligonucleotides using magnetic cycling. The method entails contacting a template oligonucleotide linked to a magnetically responsive particle with a primer oligonucleotide immobilized to a substrate and incubating under suitable hybridizing and polymerizing conditions as described above. Once an elongated capture oligonucleotide duplex has been formed, the duplex is disrupted using magnetic attraction forces effective to pull the magnetically responsive particle-bound template from the capture oligonucleotide sequence. An expanded population of immobilized capture oligonucleotides is generated by using magnetic cycling, whereby the hybridization, polymerization and duplex disruption steps are continuously cycled. This process results in a large number of immobilized capture oligonucleotides of enhanced specificity which are suitable for use in highly sensitive hybridization assays, such as in hybridization detection assays for detecting target nucleic acids in clinical diagnosis or the like.

In yet a further embodiment, an assay method is provided for detecting a nucleic acid analyte in a sample. The assay method initially entails the provision of an immobilized capture oligonucleotide, or an expanded population of such oligonucleotides, using the methods of the present invention. In this manner, the capture oligonucleotide is selected to correspond to unique DNA or RNA target nucleic acids present, or suspected of being present, within a particular clinical sample. The immobilized capture oligonucleotide is then contacted with the nucleic acid sample under hybridizing conditions to form a capture-analyte complex. After a washing process has been carried out which is sufficient to substantially remove unbound analyte, the presence of the target nucleic acid analyte may be determined by means of a detectably labeled moiety capable of selectively binding to the capture-analyte hybrid while not substantially binding to single-stranded moieties.

Accordingly, it is an object of the invention to provide a number of methods for synthesizing immobilized capture oligonucleotides which are suitable for use in highly specific and sensitive hybridization assays, such as in hybridization detection assays for detecting target nucleic acids in a clinical diagnosis or the like.

DETAILED DESCRIPTION OF THE INVENTION

The practice of the present invention will employ, unless otherwise indicated, conventional techniques of molecular biology, microbiology, recombinant DNA technology, and immunology, which are within the skill of the art. Such techniques are explained fully in the literature. See, e.g., Sambrook, Fritsch & Maniatis, *Molecular Cloning: A Laboratory Manual*, Second Edition (1989); *Oligonucleotide Synthesis* (M. J. Gait ed. 1984); *Immobilized Cells and Enzymes* (IRL press, 1986); the series, *Methods In Enzymology* (S. Colowick and N. Kaplan eds., Academic Press, Inc.); and *Handbook of Experimental Immunology*, Vols. I–IV (D. M. Weir and C. C. Blackwell eds., 1986, Blackwell Scientific Publications).

A. Definitions:

Before the invention is described in detail, it is to be understood that this invention is not limited to specific oligonucleotides, nucleotide-support attachment methods, particular magnetically responsive particles, or coating techniques, as such may vary. It is also to be understood that the terminology used herein is for the purpose of describing particular embodiments only and is not intended to be limiting.

It must be noted that, as used in the specification and the appended claims, the singular forms "a", "an" and "the" include plural referents unless the context clearly dictates otherwise. Thus, for example, reference to "an oligonucleotide" or "a hybridized complex" includes two or more such moieties, reference to "a nucleic acid analyte" includes mixtures of two or more nucleic acid analytes, and the like. In this regard, it is important to note that the techniques of the present invention may be used to provide elongated nucleotides immobilized on a solid substrate which may be used to determine the presence of a target nucleic acid analyte in a sample.

In this specification and in the claims which follow, reference will be made to a number of terms which shall be defined to have the following meanings:

As used herein, the terms "oligonucleotide" and "polynucleotide" shall be generic to polydeoxyribonucleotides (containing 2-deoxy-D-ribose), to polyribonucleotides (containing D-ribose), to any other type of polynucleotide which is an N-glycoside of a purine or pyrimidine base, and to other polymers containing nonnucleotidic backbones, providing that the polymers contain nucleobases in a configuration which allows for base pairing and base stacking such as is found in DNA and RNA. There is no intended distinction in length between the term "polynucleotide" and "oligonucleotide," and these terms may be used interchangeably. These terms refer only to the primary structure of the molecule. Thus, these terms include double- and single-stranded DNA, as well as double- and single-stranded RNA and DNA:RNA hybrids, and also include known types of modifications, for example, labels which are known in the art.

The terms "nucleoside" and "nucleotide" as used herein intend those moieties which contain not only the known purine and pyrimidine bases, but also other heterocyclic bases which have been modified. Such modifications include methylated purines or pyrimidines, acylated purines or pyrimidines, or other heterocycles known in the art.

The terms "analyte" and "nucleic acid analyte" refer to a single- or double-stranded nucleic acid molecule which contains a target nucleotide sequence. The analyte nucleic acids may be from a variety of sources, e.g., biological fluids or solids, food stuffs, environmental materials, etc., and may be prepared for hybridization analysis by a variety of means, e.g., using proteinase K/SDS, chaotropic salts, or the like. The term "nucleotide analyte" is used interchangeably herein with the terms "analyte," "nucleic acid analyte," "target" and "target molecule."

As used herein, the terms "target region" or "target nucleotide sequence" refers to a probe binding region contained within the target molecule. The term "target sequence" refers to a sequence with which a probe will form a stable hybrid under suitable hybridization conditions.

As used herein, the term "probe" refers to a structure comprised of a oligonucleotide, as defined above, which contains a nucleic acid sequence complementary to a nucleic acid sequence present in another molecule of interest. The polynucleotide regions of probes may be composed of DNA, and/or RNA, and/or synthetic nucleotide analogues.

The term "primer" is used herein to refer to a single-stranded oligonucleotide, generally of short sequence, which is capable of hybridizing with complementary sequences on DNA and RNA templates and which serves as a primer for the synthesis of a complementary DNA strand by a DNA polymerase. The primer may be composed of DNA, RNA, and/or synthetic nucleotide analogues.

Two nucleotide sequences are "complementary" to one another when those molecules share base pair organization homology. "Complementary" nucleotide sequences will combine with specificity to form a stable duplex under appropriate hybridization conditions. Thus, two sequences need not have perfect homology to be "complementary" under the invention, and in most situations two sequences are sufficiently complementary when at least about 85% (preferably at least about 90%, and most preferably at least about 95%) of the nucleotides match over a defined length of the molecule. DNA sequences that are complementary can be identified using Southern blot hybridization under, for example, stringent conditions as defined for that particular system. Southern, E. (1975) *J. Mol. Biol.* 98:503. Defining appropriate hybridization conditions is within the skill of the art. See, e.g., Sambrook, Fritsch & Maniatis, *Molecular Cloning: A Laboratory Manual*, Second Edition (1989).

As used herein, the terms "label" and "detectable label" refer to a molecule capable of detection, including, but not limited to, radioactive isotopes, fluorescers, chemiluminescers, enzymes, enzyme substrates, enzyme cofactors, enzyme inhibitors, dyes, metal ions, metal sols, ligands (e.g., biotin or haptens) and the like. The term "fluorescer" refers to a substance or a portion thereof which is capable of exhibiting fluorescence in the detectable range. The term "cofactor" is used broadly herein to include any molecular moiety which participates in an enzymatic reaction. Particular examples of labels which may be used under the invention include fluorescein, rhodamine, dansyl, umbelliferone, Texas red, luminol, NADPH, $\alpha$-$\beta$-galactosidase and horseradish peroxidase.

The term "detectably labeled analyte-binding molecule" intends a molecule which includes one or more labels capable of directly or indirectly providing for a detectable signal. The "analyte-binding molecule" intends any molecule which is capable of binding to a target analyte nucleotide. Such molecules may recognize general structural features of the target analyte, i.e., they may bind to single-stranded or double-stranded oligonucleotides, or they may recognize specific nucleotide sequences in the target analyte. Detectable labels may be bound to individual analyte-binding molecules either covalently or noncovalently, and various methods of attaching labels to moieties such as nucleotide sequences are generally known in the art. See, e.g., Leary et al. (1983) *Proc. Natl. Acad. Sci. USA* 80:4045; Renz et al. (1984) *Nucl. Acids Res.* 12:3435 and Smith et al. (1985) *Nucl. Acids Res.* 13:2399. Particularly preferred analyte-binding molecules useful in conjunction with the invention are capable of selectively binding to the hybrid formed between a probe and a target nucleic acid analyte while not substantially binding to single-stranded nucleic acids. Accordingly, immobilized hybrids to which the analyte-binding molecule has bound may be separated from unbound molecules, and the presence of the label detected. Not being limited to any particular embodiment, the analyte-binding molecule may conveniently be an antibody or fragment thereof selective for a hybrid of interest. Such moieties may be selected from antibodies to DNA:RNA, RNA:RNA or DNA:DNA hybrids. See, e.g., U.S. Pat. No. 4,623,627.

A target oligonucleotide, either single-stranded or double-stranded, or fragments thereof, can be used as an antigen to produce antibodies, either polyclonal, monoclonal, or both, by methods which are well known in the art. If polyclonal antibodies are desired, a selected mammal, (e.g., mouse, rabbit, goat, horse, pig, etc.) is immunized with a selected antigen or a fragment thereof. Serum from the immunized animal is collected and treated according to known procedures. If serum containing polyclonal antibodies is used, the polyclonal antibodies can be purified by immunoaffinity chromatography, using known procedures.

Monoclonal antibodies to a particular oligonucleotide analyte can also be readily produced by one skilled in the art. The general methodology for making monoclonal antibodies by using hybridoma technology is well known. Immortal antibody-producing cell lines can be created by cell fusion, and also by other techniques such as direct transformation of B lymphocytes with oncogenic DNA or transfection with Epstein-Barr virus. See, e.g., M. Schreier et al., *Hybridoma Techniques* (1980); Hammerling et al., *Monoclonal Antibodies and T-cell Hybridomas* (1981); Kennett et al., *Monoclonal Antibodies* (1980); see also U.S. Pat. Nos. 4,341,761; 4,399,121; 4,427,783; 4,444,887; 4,452,570; 4,466,917; 4,472,500, 4,491,632; and 4,493,890. Panels of monoclonal antibodies produced against the antigen of interest, or fragments thereof, can be screened for various properties, e.g., for isotype, epitope, affinity, etc.

The term "substrate," used interchangeably herein with the terms "support" and "solid substrate," is used to denote any solid support suitable for immobilizing an oligonucleotide. The "substrate" may be selected from a wide variety of materials including, but not limited to, fused silica (e.g., glasses), polyamides, polyesters, polyolefins, polypropylene, polytetrafluoroethylene and the like. Particularly preferred substrates include polystyrene, to which short oligonucleotides may readily be covalently attached (Letsinger et al. (1975) *Nucl. Acids Res.* 2:773–786), polyacrylamide (Gait et al. (1982) *Nucl. Acids Res.* 10:6243–6254), silica (Caruthers et al. (1980) *Tetrahedron Letters* 21:719–722), and controlled-pore glass (Sproat et al. (1983) *Tetrahedron Letters* 24:5771–5774). In particular embodiments, the "substrate" may comprise a "reaction surface" such as a fused silica slide or the like on which hybridization and polymerization reactions may be performed. A "substrate" may also preferably be the surface of a "reaction vessel," which is used in its broadest sense to include any means of containment such as cuvettes, capillaries, microtitre plates, borosilicate glass containers, polypropylene or polycarbonate test tubes or the like.

The term "magnetically responsive particle" as used herein includes any particle dispersible or suspendable in aqueous media without significant aggregation and separable from suspension by application of a magnetic field. Such particles are generally formed from a magnetic metal oxide core encased by an adsorptively or covalently bound coat and are well known in the art (see, e.g., U.S. Pat. No. 4,672,040 to Josephson). Magnetically responsive particles are commercially available from, for example, DYNAL®, Inc. (Lake Success, N.Y.) and Bangs Laboratories, Inc. (Carmel, Ind.). Such particles may be coated with divinylbenzene, polystyrene, or other polymers, copolymers, and terpolymers, and have —COOH or —NH$_2$ surface groups, or other defined chemical functionalities such as aldehyde, aliphatic amine, amide, aromatic amine, haloalkyl, hydrazide or hydroxyl by which biomolecules may be covalently, ionically, adsorptively or otherwise bound. The particles are magnetic, paramagnetic or otherwise responsive to an applied magnetic field, and preferably are "superparamagnetic," which characteristic is defined herein as responsiveness to a magnetic field without resultant permanent magnetization. The preferred size of magnetically responsive particle under the invention ranges from 0.5 to 5.0 µ. The particles preferably have an iron oxide content of approximately 10% to 60% by weight and a surface —COOH content of between about 20 to 200 µequivalents per gram of particles.

The source of the magnetic field used to manipulate the magnetically responsive particles may be a permanent magnet, e.g., a ferro- or ferri magnetic material, or an induced magnet, i.e., an electromagnet. One such magnet is a neodymium-iron-boron permanent magnet (DYNAL®, Inc.).

B. General Methods:

In one aspect of the invention, a method is provided for synthesizing immobilized capture oligonucleotides. In general, the method is directed toward synthesizing capture oligonucleotides suitable for use in highly specific and sensitive hybridization assays toward target nucleic acids in clinical diagnosis and the like.

Initially, a primer oligonucleotide is provided having a portion complementary to a template nucleic acid sequence. The primer oligonucleotide may be composed of DNA, RNA, and/or synthetic nucleotide analogues, and the sequence may be derived from a natural or synthetic source. If a natural nucleic acid sequence is used, the nucleotide may be isolated from a variety of biological sources using methods well known in the art such as by the chemical action of detergents, bases, acids, chaotropic salts or mixtures thereof. If desired, the average size of the nucleic acid sequence may be decreased by enzymatic, physical or chemical means, e.g., using restriction enzymes, sonication, chemical degradation and the like. Alternatively, the primer oligonucleotides may be synthetically derived, using a combination of solid phase direct oligonucleotide synthesis chemistry and enzymatic ligation methods which are conventional in the art. Synthetic sequences may be constructed having features such as restriction enzyme sites and may be prepared using commercially available oligonucleotide synthesis devices such as those devices available from Applied Biosystems, Inc. (Foster City, Calif.).

The oligonucleotide primers will generally be used in single-stranded form. Thus, where the sequence has been synthetically derived, denaturation will not generally be required. If the sequence has been isolated in double-stranded form, denaturation to single-stranded form may be accomplished using various techniques known in the art, such as treatment with alkali, hydroxide, formamide, detergent, heat, or combinations thereof. Further, the oligonucleotide primer will have a complementary sequence to a template analyte, ranging from 5 to 500 bases, more preferably from 5 to 200, and most preferably from 10 to 50 bases in length. The primer may further have an attachment sequence generally 6 to 20 bases in length, and typically 6 to 10 bases in length. The optional attachment sequence serves as a point of attachment of the primer moiety to a support and may be either 3' or 5' to the complementary sequence.

The primer sequence thus derived is then immobilized to a solid support or substrate. Particularly preferred supports include materials such as polystyrene, polycarbonate, polyacrylamide, polypropylene, polytetrafluoroethylene, silicas, fused silicas, and the like. In preferred embodiments, the substrate will be a reaction surface such as a fused silica slide. Most conveniently, the substrate is the surface of a reaction vessel in which the subsequent steps of the method may be performed. Thus, supports particularly suited for the invention include cuvettes, capillaries, microtitre plates, borosilicate glass containers, polypropylene or polycarbonate test tubes and the like. The surfaces of the support may be subjected to surface modification such as silanization to facilitate attachment of the primer sequence thereto.

Immobilization of the primer sequence to a suitable substrate may be performed using conventional techniques. See, e.g., Letsinger et al. (1975) *Nucl. Acids Res.* 2:773–786, and "Oligonucleotide Synthesis, a Practical Approach," Gait, M. J. (ed.), Oxford, England: IRL Press (1984). The surface of a substrate may be treated with an organosilane coupling agent to functionalize the surface. The organosilane coupling agent is preferably represented by the formula $R_n SiY_{(4-n)}$ wherein: Y represents a hydrolyzable group, e.g., alkoxy, typically lower alkoxy, acyloxy, lower acyloxy, amine, halogen, typically chlorine, or the like; R represents a nonhydrolyzable organic radical that possesses a functionality which enables the coupling agent to bond with organic resins and polymers; and n is 1, 2 or 3, usually 1. One example of such an organosilane coupling agent is 3-glycidoxypropyltrimethoxysilane "GOPS"), the coupling chemistry of which is well-known in the art. See, e.g., Arkins, "Silane Coupling Agent Chemistry," *Petrarch Systems Register and Review*, Eds. Anderson et al. (1987). Other examples of organosilane coupling agents are (γ-aminopropyl)triethoxysilane and (γ-aminopropyl) trimethoxysilane. Still other suitable coupling agents are well known to those skilled in the art. Thus, once the organosilane coupling agent has been covalently attached to the support surface, the agent may be derivatized, if necessary, to provide for surface functional groups. In this manner, support surfaces may be coated with functional groups such as amino, carboxyl, hydroxyl, epoxy, aldehyde and the like.

Use of the above functionalized coatings on a solid support provides a means for selectively attaching oligonucleotides to the support. Thus, an oligonucleotide primer may be provided with a 5'-terminal amino group which can be reacted to form an amide bond with a surface carboxyl using carbodiimide coupling agents. Attachment to the 5' terminus of the oligonucleotide may also be effected using surface hydroxyl groups activated with CNBr to react with 5'-terminal amino groups. 3'-Terminal attachment of an oligonucleotide primer may be effected using, for example, a hydroxyl or protected hydroxyl surface functionality.

Continuing with the method, a template oligonucleotide sequence is provided wherein a portion of the template is complementary to the primer oligonucleotide sequence. More particularly, the selected template oligonucleotide contains a sequence ranging from 7 to 25 bases, more preferably from 10 to 20 bases, and most preferably from 15 to 20 bases, which is complementary to the immobilized primer. The template sequence may be of natural or synthetic origin and obtained using the methods as just described. The template is immobilized to a retrievable support such as a magnetically responsive particle. In a preferred embodiment, the selected magnetically responsive particle may be a latex particle made of divinylbenzene, polystyrene, or other polymers, copolymers, and terpolymers, having —COOH or —NH$_2$ surface groups or other defined chemical functionalities such as aldehyde, aliphatic amine, amide, aromatic amine, haloalkyl, hydrazide or hydroxyl by which oligonucleotides may be covalently, ionically, adsorptively or otherwise bound. The particles are magnetic, parmagnetic, superparamagnetic, or otherwise responsive to an applied magnetic field.

The oligonucleotide template may be readily attached to a magnetically responsive latex particle by adsorption through electrostatic and/or hydrophobic interactions. However, covalent attachment of the nucleotide to the particle is preferred, and a wide variety of covalent coupling techniques are known in the art. One such method involves introduction of diazonium groups onto the latex and subsequent reaction with the guanine, thymine, and uracil residues of the polynucleotide. Noyes et al. (1975) *Cell* 5:301–310. Phosphate ester groups can be introduced onto the latex and coupled to the probe through activation with carbodiimide. Bautz et al. (1962) *Proc. Nat'l Acad Sci. USA* 48:400–408. Hydroxyl groups on the latex can be used with coupling through phosphodiester links formed between the terminal phosphate of the polynucleotide and the surface bound hydroxyls using water soluble carbodiimide activation, (Rickwood, D. (1972) *Biochem Biophys. Acta* 269:47–50), or by coupling nucleophilic sites on the polynucleotide with cyanogen bromide activated hydroxyls. Arndt-Jovin et al. (1975) *Eur J. Biochem.* 54:411–418. The 3'-hydroxyl terminus of an RNA probe can be oxidized with periodate and coupled by Schiff base formation with a latex particle bearing amine or hydrazide groups. Gilham, P. T. (1971) *Meth. Enzymol.* 21:191–197. Latexes with nucleophilic sites can be reacted with cyanuric chloride and then coupled to a selected polynucleotide. Hunger et al. (1981) *Biochem. Biophys. Acta* 653:344–349. Photoactivatable groups can be introduced onto the latex, and oligonucleotides can then be coupled by activation with light. U.S. Pat. No. 4,542,102 to Dattagupta.

Once the immobilized template sequence has been thus prepared, it is contacted with the primer oligonucleotide described above in a reaction vessel and incubated under suitable hybridization conditions. In one particular embodiment, the primer oligonucleotide is immobilized to the reaction vessel surface as previously described. Hybridization between the template and the primer oligonucleotide sequence to form a template-hybrid complex generally takes from about 30 minutes to about 2 hours. The hybridization occurs at the highest rate approximately 25° C. below the temperature $T_m$, at which the nucleotide hybrid is 50% melted. The $T_m$ for a particular hybridization pair will vary with the length and nature of the nucleotides and may be readily determined by those of ordinary skill in the art.

In general, hybridization is carried out in a buffered aqueous medium typically formulated with a salt buffer, detergents, nuclease inhibitors and chelating agents, using techniques well-known to those skilled in the art. Such formulations may be selected to preclude significant non-specific binding of nucleotides with the support surface. Depending on the nature of the particular oligonucleotide binding pair, various solvents may be added to the medium such as formamide, dimethylformamide and dimethylsulfoxide, and the stringency of the hybridization medium may be controlled by temperature, pH, salt concentration, solvent system, or the like. Defining appropriate hybridization conditions is within the skill of the art. See, e.g., Sambrook, Fritsch & Maniatis, *Molecular Cloning: A Laboratory Manual*, Second Edition (1989).

Once hybridization is complete, and the template-primer complex has been formed, the complex is available as a primer for the synthesis of a complement to the template nucleic acid sequence as described in Smith, M., "Methods of RNA and DNA Sequencing," Wasserman, S. M. (ed.), Praeger Scientific, NY (1983). Thus, after washing the template-primer complex with a suitable aqueous wash (i.e., formulated generally with a salt buffer and detergents effective to keep the hybrid immobilized while permitting the removal of unhybridized species), a polynucleotide polymerase is added under suitable polymerization conditions such that the immobilized primer is extended to provide an elongated capture oligonucleotide complementary to the template sequence. A number of in vitro oligonucleotide synthesis techniques are known in the art, and defining suitable polymerization conditions is within the skill of the art. See, e.g., Sambrook et al., supra.

Once the elongated capture oligonucleotide has been polymerized, the capture-template duplex is disrupted using magnetic attraction forces effective to pull the magnetically responsive particle-bound template oligonucleotide away from the newly formed complementary capture oligonucleotide sequence. Duplex disruption may be readily effected by applying a magnetic field to the periphery of the reaction vessel for a period of time effective to separate the duplex. Thus, the magnetic field must be of sufficient strength to overcome the complementary base-pair binding forces and is generally in the range of about 100–1000 Oersteds. The source of the magnetic field may be a permanent magnet, e.g., a ferro- or ferromagnetic material, or an induced magnet, i.e., an electromagnet. The particle-bound template oligonucleotide may then be substantially removed from the reaction vessel using magnetic attraction, filtration techniques, or any combination thereof.

Accordingly, after the removal of the magnetically responsive particle-bound template oligonucleotide, the elongated support-immobilized capture oligonucleotide is available for use in highly specific and sensitive hybridization assays toward target nucleic acids in clinical diagnosis and the like.

In another embodiment of the invention, a method is provided for synthesizing an expanded population of immobilized capture oligonucleotides using magnetic cycling.

More particularly, a method is provided wherein a template oligonucleotide linked to a magnetically responsive particle is contacted with a primer oligonucleotide immobilized to a substrate. Suitable substrates include materials such as, but not limited to, polystyrene, polycarbonate, polyacrylamide, polypropylene, polytetrafluoroethylene, silicas, fused silicas, and the like. In some cases, the substrate will be a reaction surface such as a fused silica slide. Most conveniently, the substrate is the surface of a reaction vessel in which the subsequent steps of the method may be performed.

The immobilized primer sequence is selected such that it is complementary to a portion of the template oligonucleotide. Attachment of the primer to the substrate, and of the template to the magnetically responsive particle, is carried out as described above. The primer and template oligonucleotides are incubated together under suitable hybridizing conditions whereby a template-primer complex is formed. The complex is then available to serve as a primer for the synthesis of a complementary strand to the template nucleic acid sequence.

Continuing with the method, the template-primer complex is generally washed with a suitable aqueous wash to remove nonhybridized moieties, and the complex contacted with a polynucleotide polymerase under suitable polymerization conditions such that the immobilized primer is extended to provide an elongated capture oligonucleotide complementary to the template sequence. Once the elongated capture oligonucleotide has been formed, the capture-template duplex is disrupted using magnetic attraction forces effective to pull the magnetically responsive particle-bound template oligonucleotide away from the newly formed complementary capture oligonucleotide sequence.

An expanded population of immobilized capture oligonucleotides may be generated under the method by using magnetic cycling wherein the hybridization, polymerization and disruption steps are continuously cycled. More particularly, a magnetic field applied to the periphery of the reaction vessel is initially used to disrupt the first capture-template duplex. As will be readily appreciated by those of skill in the art, the magnetic force may be maintained to retain the particle-bound template oligonucleotides within the reaction vessel while washing, aspiration, decanting and like operations are performed. Thus, once suitable hybridization conditions have been re-established, the magnetic force is removed, releasing the particle-bound template into solution where it is available to hybridize with a second support-bound primer. A second template-primer complex is thus formed and serves as a primer for the synthesis of another complementary strand to the template nucleic acid sequence once suitable polymerization conditions have been re-established. In this manner, continued cycling of the above steps results in a large number of immobilized primer oligonucleotides being elongated to provide an expanded population of immobilized capture oligonucleotides.

In yet another embodiment of the invention, an assay method is provided for detecting a nucleic acid analyte in a sample. The assay method is initialized by synthesizing a capture oligonucleotide conveniently immobilized to a substrate using the methods described above. In a preferred embodiment, the capture oligonucleotide is immobilized to the surface of a reaction vessel in which the remaining steps of the assay may be carried out. The particular template oligonucleotide which is used to synthesize the capture oligonucleotide may be selected so as to be complementary to any of a wide variety of target nucleic acids. Thus, target nucleotides corresponding to unique DNA or RNA sequences or specific genes may be selected where it is desired to detect the presence of genetic disease, conditions such as sickle cell anemia, tissue compatibility, cancer or precancerous states, or bacterial or viral infection.

Once an appropriate target nucleic sequence is selected and the complementary capture oligonucleotide has been immobilized to a substrate, a capture step is carried out wherein a nucleic acid analyte containing or suspected of containing the target oligonucleotide is contacted with the capture sequence under suitable hybridizing conditions to form a capture-analyte complex. Hybridization of the capture-analyte complex is carried out as described above in regard to the capture synthesis methods. The nucleic acid analyte may be prepared using techniques known in the art.

Particularly, a clinical sample of, for example, cells containing or suspected of containing a target nucleic acid analyte is provided. The subject analyte is selected as being indicative of an particular infectious agent, genetic condition, or gene characteristic. The clinical sample may be derived from a variety of sources, e.g., human or other mammalian biological fluids or tissues, including blood (serum or plasma), urine, cerebrospinal fluid, stool, sputum, or wound exudates, ocular lens fluid, lymph fluid, genital washings, biopsy tissue samples, food stuffs and environmental materials. Biopsy tissue samples may be reduced to single cell suspensions using techniques known in the art such as physical maceration, sonication, centrifugation or the like.

The cell samples are treated to release DNA and/or RNA. Chemical lysing may be performed under the invention using dilute aqueous alkali, e.g., 0.1 to 1.0M sodium hydroxide. The alkali serves to denature the DNA or RNA. Further methods of denaturation and cell lysing are known in the art and may employ, among other things, elevated temperature, organic reagents (e.g., alcohols, amides, ureas, phenols and sulfoxides), inorganic ions (chaotropic salts such as sodium trifluoroacetate, sodium trichloroacetate, sodium perchlorate, guanidinium isothiocyanate, sodium iodide, potassium iodide, sodium isothiocyanate and potassium isothiocyanate) and combinations thereof.

If desired, the released DNA and/or RNA may be extracted from the sample and purified using methods well known in the art such as by density gradient centrifugation, ethanol precipitation, phenol extraction and the like. See, e.g., Sambrook, Fritsch & Maniatis, *Molecular Cloning: A Laboratory Manual*, Second Edition (1989). Additionally, the DNA and/or RNA may be digested using restriction endonucleases to provide smaller nucleotide segments.

Proceeding with the method, after the nucleic acid analyte and capture oligonucleotides have been incubated under suitable hybridization conditions for a sufficient time to allow formation of a capture-analyte complex, a washing step is performed to provide an immobilized capture-analyte complex substantially free of unbound analyte. In this manner, the presence of the target nucleic acid analyte may be determined using a detection step of contacting the complex with a detectably labeled moiety and detecting the mount of bound or unbound label. The detection step is generally carried out under suitable conditions, such as in a detection solution formulated according to a particular detection means (e.g., where the label employed is an enzyme, the solution is formulated to include the selected enzyme substrate and any necessary reagents). A wide variety of methods of detectably labeling target oligonucleotides are known in the art. See, e.g., Dunn et al. (1980) *Methods Enzymol.* 5:468–478; Palva et al. (1983) *Journal Clin. Micro.* 18:92–100; Ranki et al (1983) *Gene* 1:77–85;

Polsky-Cynkin et al. (1985) *Clin. Chem.* 31:1438–1443; and U.S. Pat. Nos. 4,486,539 and 4,563,419. Further, depending on the nature of the label, a number of techniques to detect the presence of the label are known in the art, e.g., fluorometric, spectrophotometric and visual (e.g., colorimetric or chemiluminescence) techniques.

Particularly preferred detection methods employ a detectably labeled analyte-binding molecule which is capable of selectively binding the capture-analyte complex while not substantially binding single-stranded nucleic acids. Thus, an antibody, or fragment thereof specific for the capture-analyte complex may be provided using a variety of methods known in the art such as those described in U.S. Pat. No. 4,623,627. The anti-complex antibody may be labeled with a suitable detectable chemical group, such as an enzyme, fluorescer, chromophore, luminescer or ligand for rapid and sensitive detection. Other preferred detecting methods employ delectably labeled oligonucleotides complementary to a sequence present in the target nucleic acid analyte. Accordingly, a method has been described for a reliable and convenient nucleic acid diagnostic assay which is useful for clinical diagnosis such as in the detection of disease in a particular human or other mammalian subject.

It is to be understood that while the invention has been described in conjunction with the preferred specific embodiments thereof, that the description above as well as the example which follows are intended to illustrate and not limit the scope of the invention. Other aspects, advantages and modifications within the scope of the invention will be apparent to those skilled in the art to which the invention pertains.

The following examples are put forth so as to provide those of ordinary skill in the art with a complete disclosure and description of how to use the method of the invention, and is not intended to limit the scope of what the inventor regards as her invention. Efforts have been made to ensure accuracy with respect to numbers (e.g., amounts, temperature, etc.) but some errors and deviations should be accounted for. Unless indicated otherwise, parts are parts by weight, temperature is in °C. and pressure is at or near atmospheric.

EXAMPLE 1

A. Synthetic DNA oligonucleotides, Oligo A (a 24 mer) and Oligo B (a 36 mer having a complementary 17 base pair sequence to Oligo A and a sequence which is not complementary to Oligo A) are respectively used as a primer immobilized to a substrate and a template linked to a magnetically responsive particle. Oligo A and B are prepared using an automated phosphoramidite method as described by Warner et al. (1984) *DNA* 1:401, and purified using techniques well known in the art.

B. Oligo A is immobilized to a silica substrate which is prepared as follows. A silane coupling agent is deposited from aqueous alcohol solution onto a fused-silica substrate. A 95% ethanol-5% water solution is adjusted to pH 4.5–5.5 with acetic acid. Silane is added with stirring to yield a 2% final concentration. At least about 5 minutes is allowed for hydrolysis and silanol formation. The substrate is then dipped into the solution, agitated gently, and removed after 1–2 minutes. The substrate is rinsed free of excess materials by dipping briefly in ethanol. Cure of the silane layer is for 5–10 minutes at 110° C. or for 24 hours at room temperature (<60% relative humidity). Any silane coupling agent may be used having the general formula:

$R_n SiX_{4-n}$ wherein X is the hydrolyzable group involved in the reaction with the inorganic fused-silica substrate and may comprise, for example, a halogen atom;

the Si-X bond is replaced by the Si-substrate bond; and

R is a nonhydrolyzable organic radical that possesses a functionality which enables the coupling agent to covalently bond to the Oligo A.

The Oligo A is covalently attached to the silica substrate using any standard technique. Typically, substituted alkyl or aryl silyl compounds will be used to form a siloxane or siloximine linkage, and the oligonucleotide will thus be bound to the support therethrough.

C. Oligo B is 5'-$NH_2$ modified for attachment to carboxyl beads. Amino groups are introduced at the 5'-end of Oligo B using the one-step method described by Chu et al. (1985) *DNA 4:327–331*. This results in a greater nucleophilicity in the terminal primary amino group of the alkyl linker relative to the amino functionalities of the bases. The modified Oligo B DNA is then precipitated with ethanol and lyophilized before reaction with the carboxyl beads.

Magnetically responsive particles having carboxyl surface functionalities are available from DYNAL®, Inc., Lake Success, N.Y. or Bangs Laboratories, Inc., Carmel, Ind.

The method proceeds as follows, 100 µg of the modified Oligo B is dissolved in 500 µl 0.1M imidazole buffer pH 7 (1-methylimidazole, Sigma, St. Louis, Mo.), 0.1M EDC (1-ethyl-3-dimethylaminopropyl) carbodiimide (Sigma, St. Louis, Mo.), mixed with 5 mg of particles having carboxyl surface functionalities, and incubated for 20 hours at room temperature with gentle shaking.

D. Once the immobilized Oligo A template and the particle-linked Oligo B primer have been prepared, the two species are contacted and incubated under suitable hybridization conditions. The hybridization proceeds as follows, prehybridization of the oligomers is carried out in 300 µl 5× SSPE (20× SSPE consists of 0.17M phosphate buffer, pH 7.4, 3M NaCl, and 0.02M EDTA), 10× Denhardt's solution (50× Denhardt's consists of 5 g Ficoll, 5 g polyvinylpyrrolidone and 5 g BSA in 500 ml $H_2O$), 0.1% SDS and 300 µg sonicated and denatured ctDNA. Prehybridization is carried out for 30–60 minutes at 37° C. with gentle shaking. Hybridization is carried out in 300 µl of the same solution (without the ctDNA) for 1–2 hours at 37° C. with gentle shaking. After hybridization, the duplexes are washed with a solution of 3×1 ml 2× SSC and 0.05% SDS at room temperature to yield a 17 base pair hybridized complex having a single stranded overhang corresponding to the noncomplementary sequence of the Oligo B.

E. Once hybridization has been effected, suitable polymerization conditions are established by adding to the complex a mixture of deoxynucleotides and DNA polymerase enzyme and then incubating at a temperature determined by the length and composition of Oligo A and B. The single-stranded DNA of Oligo B serves as the template, whereas the Oligo A serves as a primer. The duplex which is thus polymerized is then disrupted using magnetic forces effective to pull the magnetically responsive particle-bound Oligo A away from the newly formed complementary oligonucleotide sequence.

Thus, the newly elongated Oligo B is then available for use in highly specific and sensitive hybridization assays toward target nucleic acids in clinical diagnosis and the like.

I claim:

1. An assay method for detecting a nucleic acid analyte in a sample, comprising:

(a) a capture oligonucleotide synthesis step of: (i) contacting a template oligonucleotide complementary to a target oligonucleotide and linked to a magnetically responsive particle with a primer oligonucleotide immobilized to a substrate, said primer oligonucleotide being complementary to a portion of the template oligonucleotide; (ii) incubating the template oligonucleotide and the primer oligonucleotide under hybridizing conditions to form a template-primer complex; (iii) adding a polynucleotide polymerase under polymerization conditions, whereby the primer oligonucleotide is extended to provide an immobilized capture oligonucleotide complementary to the template oligonucleotide; (iv) applying an electromagnetic field effective to de-hybridize the template oligonucleotide from the capture oligonucleotide; and (v) washing the immobilized capture oligonucleotide;

(b) a capturing step of: (i) contacting the immobilized capture oligonucleotide synthesized in step (a) with a nucleic acid analyte containing or suspected of containing the target oligonucleotide; (ii) incubating the capture oligonucleotide with the nucleic acid analyte under hybridizing conditions to form a capture oligonucleotide-analyte complex; and (iii) washing to provide an immobilized capture oligonucleotide-analyte complex substantially free of unbound analytes; and (c) a detecting step of: (i) contacting the immobilized capture oligonucleotide-analyte complex obtained in step (b) with a detectably labeled analyte-binding molecule; and (ii) detecting the amount of bound or unbound label.

2. The method of claim 1 wherein the analyte-binding molecule comprises an oligonucleotide probe complementary to a portion of the hybridized capture oligonucleotide-analyte complex.

3. The method of claim 1 wherein the detectable label is a fluorescer or an enzyme.

4. The method of claim 3 wherein the detectable label further comprises a plurality of fluorescers.

5. The method of claim 1 wherein the analyte-binding molecule comprises an antibody.

6. The method of claim 1 wherein the capture oligonucleotide synthesis step further comprises continuously cycling steps (a) through (d) such that an expanded population of immobilized capture oligonucleotides is synthesized.

7. The method of claim 1 wherein the primer oligonucleotide is covalently immobilized to the substrate.

8. The method of claim 1 wherein the primer oligonucleotide is covalently immobilized to a fused silica substrate.

* * * * *